United States Patent
Har-Noy

(10) Patent No.: US 11,037,087 B2
(45) Date of Patent: Jun. 15, 2021

(54) AUTOMATED DEVICE FOR BIOLOGIC DRUG DISTRIBUTION

(71) Applicant: Immunovative Therapies Ltd., Jerusalem (IL)

(72) Inventor: Michael Har-Noy, Jerusalem (IL)

(73) Assignee: MIRROR BIOLOGICS, INC., Mesa, AZ (US)

(*) Notice: Subject to any disclaimer, the term of this patent is extended or adjusted under 35 U.S.C. 154(b) by 203 days.

(21) Appl. No.: 16/434,977

(22) Filed: Jun. 7, 2019

(65) Prior Publication Data
US 2019/0295706 A1   Sep. 26, 2019

Related U.S. Application Data

(60) Division of application No. 15/077,493, filed on Mar. 22, 2016, now Pat. No. 10,318,712, which is a (Continued)

(51) Int. Cl.
*G16H 20/13* (2018.01)
*G07F 9/10* (2006.01)
(Continued)

(52) U.S. Cl.
CPC ............ *G06Q 10/08* (2013.01); *G05B 15/02* (2013.01); *G07F 9/105* (2013.01);
(Continued)

(58) Field of Classification Search
CPC ........ G06Q 10/08; G16H 10/40; G16H 20/13; G07F 9/105; G07F 17/0092; G05B 15/02
See application file for complete search history.

(56) References Cited

U.S. PATENT DOCUMENTS 5,713,485 A * 2/1998 Lift ..................... G07F 17/0092
                                                               221/2
6,219,587 B1 * 4/2001 Ahlin ................... G07F 17/0092
                                                               700/233
(Continued)

FOREIGN PATENT DOCUMENTS

CN          1893973 A        1/2007
TW       201130509 A         6/2011
(Continued)

OTHER PUBLICATIONS

Examination Report issued in related Taiwan patent application No. 102107555, dated Aug. 10, 2016.
(Continued)

*Primary Examiner* — Ramesh B Patel
(74) *Attorney, Agent, or Firm* — Westman, Champlin & Koehler, P.A.; Z. Peter Sawicki; Visala C. Goswitz

(57) ABSTRACT

The present disclosure relates to an apparatus for dispensing biologic drug compositions. The apparatus includes an automated device that can store a biologic drug under the desired conditions. When authorized, the automated device can process the stored biologic drug by performing the desired processing steps to prepare the biologic drug for administration to a patient. The automated device may include a computing system to transmit patient information to a remote location and receive authorization from a remote location.

16 Claims, 2 Drawing Sheets

Related U.S. Application Data continuation of application No. 13/659,290, filed on Oct. 24, 2012, now abandoned, which is a continuation of application No. PCT/US2012/055142, filed on Sep. 13, 2012.

(60) Provisional application No. 61/667,633, filed on Jul. 3, 2012, provisional application No. 61/620,651, filed on Apr. 5, 2012, provisional application No. 61/561,101, filed on Nov. 17, 2011, provisional application No. 61/534,642, filed on Sep. 14, 2011.

(51) Int. Cl.
| | | |
|---|---|---|
| *G05B 15/02* | (2006.01) | |
| *G06Q 50/22* | (2018.01) | |
| *G07F 17/00* | (2006.01) | |
| *G06Q 10/08* | (2012.01) | |
| *G16H 10/40* | (2018.01) | |

(52) U.S. Cl.
CPC ......... *G07F 17/0092* (2013.01); *G16H 10/40* (2018.01); *G16H 20/13* (2018.01)

(56) References Cited

U.S. PATENT DOCUMENTS

| | | | | |
|---|---|---|---|---|
| 6,560,973 B2* | 5/2003 | Jones | ............. | F25D 29/00 62/60 |
| 6,604,019 B2* | 8/2003 | Ahlin | ............. | G07F 7/069 700/231 |
| 7,155,306 B2* | 12/2006 | Haitin | ............. | A61G 12/001 700/242 |
| 7,483,766 B1* | 1/2009 | Frankel | ............. | G16H 20/13 700/237 |
| 7,630,789 B2* | 12/2009 | Broadfield | ............. | A61G 12/001 221/98 |
| 7,668,731 B2 | 2/2010 | Martucci et al. | | |
| 7,735,681 B2* | 6/2010 | Handfeld | ............. | G07F 9/026 221/152 |
| 7,783,379 B2* | 8/2010 | Beane | ............. | G06Q 20/12 700/237 |
| 7,801,772 B2* | 9/2010 | Woodward | ......... | G06Q 30/0635 705/26.1 |
| 10,318,712 B2* | 6/2019 | Har-Noy | ............. | G16H 20/13 |
| 2003/0088333 A1* | 5/2003 | Lift | ............. | G16H 40/67 700/237 |
| 2003/0120384 A1* | 6/2003 | Haitin | ............. | G07F 17/0092 700/242 |
| 2007/0185615 A1* | 8/2007 | Bossi | ............. | G07F 17/0092 700/244 |
| 2010/0072216 A1* | 3/2010 | Voute | ............. | A01N 1/0263 220/737 |
| 2015/0203297 A1* | 7/2015 | Manning | ............. | B65G 1/045 700/218 |

FOREIGN PATENT DOCUMENTS

| | | |
|---|---|---|
| WO | 2003/040991 A2 | 5/2003 |
| WO | 2004/100094 A2 | 11/2004 |
| WO | 2005/006647 A2 | 1/2005 |
| WO | 2005/064521 A2 | 7/2005 |
| WO | 2009061874 A1 | 5/2009 |

OTHER PUBLICATIONS

International Search Report and Written Opinion; PCT/US2012/055142, dated Feb. 14, 2013.

* cited by examiner

AUTOMATED DEVICE FOR BIOLOGIC DRUG DISTRIBUTION

CROSS-REFERENCE TO RELATED APPLICATION

This application is a Divisional of U.S. patent application Ser. No. 15/077,493, filed Mar. 22, 2016, which is a Continuation of U.S. patent application Ser. No. 13/659,290, filed Oct. 24, 2012, which is a Continuation of International Application No. PCT/US2012/055142, filed Sep. 13, 2012, in English, which claims priority to U.S. provisional application Ser. No. 61/534,642, filed Sep. 14, 2011, U.S. provisional application Ser. No. 61/561,101, filed Nov. 17, 2011, U.S. provisional application Ser. No. 61/620,651, filed Apr. 5, 2012, and U.S. provisional application Ser. No. 61/667,633, filed Jul. 3, 2012, the contents of which are hereby incorporated by reference in their entirety.

FIELD

This disclosure relates to automated devices and more particularly automated devices for use in distribution of biologic drugs.

BACKGROUND

Automated devices such as vending machines have been used for dry goods, refrigerated foods and/or frozen foods for a long time. The vending machines are placed in locations convenient to the consumer. When the consumer desires the product, he or she physically deposits cash or a credit card into the machine, makes a selection and receives the product.

More recently, automated devices have been used for conveying regulated pharmaceuticals. In acquiring regulated pharmaceuticals, a consumer in addition to providing payment must also provide documentation in some manner that they are eligible and permitted to receive the product. In this case also, the consumer physically interacts with the automated device to provide payment and permission for obtaining the product. These pharmaceuticals generally include dry or liquid pharmaceuticals and are regulated in order to prevent fraud and/or abuse.

SUMMARY

Figure 1:
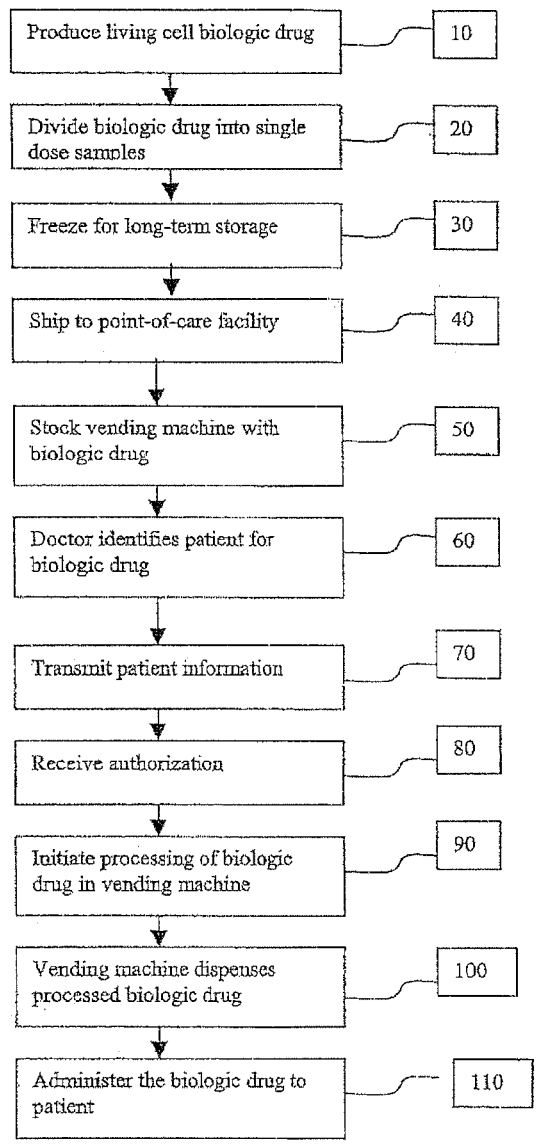
FIG. 1 is a flow chart illustrating steps in a method of distribution of the living cell biologic drug.

In a first aspect, the invention relates to an automated device comprising a storage chamber for storing a biologic sample, a processing compartment, a system for receiving authorization to transfer the biologic sample from the storage chamber to the processing compartment and a dispensing chamber for receiving the biologic sample after processing. The system for receiving authorization in the device can include a computer with an internet connection.

In another aspect, the invention relates to a method for dispensing a dose of biologic drug. The method includes storing the biologic drug in an automated device under desired conditions, and processing the biologic drug in the automated device upon receipt of authorization to process a dose of the biologic drug. The method can also include a step wherein the biologic drug is manufactured at a remote location, stored for long-term storage and transported for placement in the automated device.

In yet another aspect, the invention relates to a method for providing a biologic drug. The method includes manufacturing the biologic drug in a manufacturing facility, transporting the biologic drug to a point of care site wherein biologic drug is transported under conditions to maintain the biologic activity of the drug and storing the biologic drug in an automated device at the point of care site until a patient is authorized for receiving the biologic drug.

DETAILED DESCRIPTION OF ILLUSTRATIVE EMBODIMENTS

The present description relates to an automated device or vending machine for live biological drugs. The biologic drugs include living cells that are maintained in a frozen state in the vending machines. The vending machines are generally placed in a point-of-care site, for example, a clinic, a hospital or other healthcare setting. The vending machine may also include a connection to a remote location generally through a secure internet connection. The connection can be used to transmit patient information such as medical records and details regarding financial payment. The remote location can be anywhere in the world and can be staffed by people that can verify the patient records and collect payment for the biologic drugs or obtain sufficient information regarding commitment for payment. Once the patient is approved for receiving the biologic drug, the patient, doctor or other healthcare worker can interact with the machine directly or through the use of a computer and start the processing cycle. Alternatively, the automated device may receive a code directly from the remote site through an internet connection to start the processing of a sample of the biologic drug.

The processing cycle can include, for example, retrieving a dose of the living cell drug, thawing, washing, incubating and formulating the sample for administration to the patient. The processing cycle can have a variable time duration and can be as little as several minutes or as long as a day. In exemplary embodiments, the processing cycle may take several hours. The actual events and components involved in the processing cycle can vary and depend on the specific biologic drug dispensed and formulated for administration to a patient. Upon completion of the processing cycle by the vending machine, the biologic drug can be retrieved by a person such as a health care worker and administered to the patient. Health care workers can include a doctor, nurse, technician and the like. A patient or a layperson trained in handling the biologic drug may also retrieve the biologic drug from the automated device.

Storage and processing of the biologic drug in an automated device as described herein advantageously alleviates the patient's need to travel to a site where the biologic drug is manufactured. In other words, the method employed herein for storing and processing the biologic drug enables the drug to be manufactured anywhere in the world and be used by a patient at a point of care site anywhere in the world. In addition, since the processing of the sample is performed in an automated device there is less chance of the sample being mishandled by a worker.

The present description also includes a novel business method. This method includes preparing a frozen biologic drug in a manufacturing facility and distributing the frozen drug to point-of-care sites. The frozen biologic drug is stored in an automated device capable of maintaining the drug in a frozen state at a point of care site until needed by a patient. When a doctor prescribes the use of the biologic drug to a patient, the patient's medical information and financial payment information is transmitted over a secure link to a remote location for authorization. Upon authorization, the automated device can be activated to initiate a processing cycle to prepare the drug for administration. The doctor or other authorized healthcare worker can obtain the drug after completion of the processing cycle and administer it to the patient. Alternatively, the patient may retrieve the formulated drug from the dispensing chamber and self-administer the drug.

The biologic drugs placed in the automated devices include living cells that have been manipulated in a number of ways. These manipulations include cells that have been proliferated, differentiated, activated and the like. In some embodiments, these living cells are immune cells and other embodiments, the living cells are activated T-cells. These immune cells may have been activated as described, for example, in U.S. Pat. Nos. 7,435,592, 7,678,572 and 7,402,431 incorporated herein by reference. Living cells as described herein include cells that can be frozen, thawed and when placed in appropriate media can be viable living cells that carry out cellular functions. The cellular functions can include secretion of molecules, proliferation, differentiation and the like. The cellular functions can be carried out in vitro and/or in vivo. For purposes of this application the term cell(s) can include prokaryotic and eukaryotic cells. In some preferred embodiments, the cells are eukaryotic cells. The biologic drug generally includes human cells but cells from other animals can be amenable to frozen living cell storage.

The living cells after being manipulated in the desired manner for obtaining a biologic drug can be prepared for long-term storage by freezing in the appropriate manner. The long-term storage can include suspension of the cells in media suitable for maintaining the viability of the cells during freezing and upon thawing.

In one exemplary embodiment, the method of distributing a biologic drug is as shown in the flow chart of FIG. 1. In this method, the living cell biologic drug is prepared in a manufacturing facility meeting the appropriate standards (step 10). After manufacturing of a batch of the biologic drug, the biologic drug is divided into individual doses and placed into vials or other suitable containers (step 20). The containers with the individual doses are frozen for long-term storage (step 30), preferably at about 70° C. Some desired number of doses can be shipped to point-of-care facilities around the world (step 40). The shipping method used can maintain the cells at the desired temperature, i.e. about 70° C. The point-of-care facility, upon receiving the shipment of frozen biologic drug samples, stocks an automated device (a vending machine) already present at the site (step 50). The biologic drug is stored in the storage chamber of the vending machine at the desired temperature until needed by a patient.

In step 60, a patient, examined by a doctor, is identified to benefit from the biologic drug in the vending machine. Patient information is transmitted (step 70) to a remote location. The patient information can include, for example, patient's medical records, patient's financial, payment and/ or insurance information. Other information regarding the patient deemed necessary or useful may also be transmitted to the remote location. The patient information may be transmitted through a secure internet connection within the automated device or connected to the automated device. Alternatively, the patient information may be transmitted by a worker in the point of care facility through any other computing system with an internet connection or using other methods of information transfer, preferably in a secure manner.

In step 80, a person at a remote location receives the patient information and determines if the patient will be authorized to receive a dose of the biologic drug in the vending machine. Authorization determination can be made based on the patient medical condition, payment from the patient, and/or commitment of payment from the patient. Once the patient is approved for receiving the biologic drug, the point-of-care facility is notified and given permission to start the processing cycle of the frozen biologic drug (step 90). The point-of-care facility, for example, may be given a code that must be entered into the vending machine for the processing cycle to begin. Upon entering the code, one dose of the biologic drug is moved from the storage chamber to the processing compartment(s) (step 90). After the processing, the formulated drug is dispensed from the vending machine (step 100), removed and administered to the patient (step 110).

Figure 2:
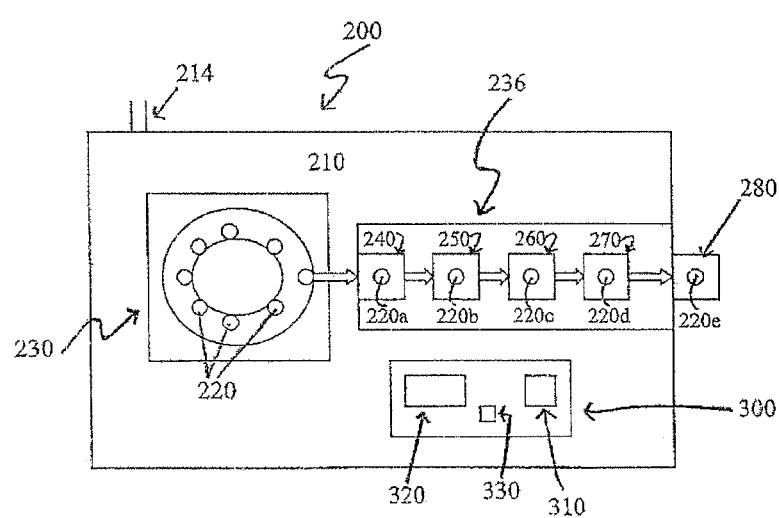
FIG. 2 is a schematic drawing of some of the main components of one embodiment of a vending machine of the present invention.

In an exemplary embodiment as shown in FIG. 2, vending machine (200) includes storage chamber 210 holding multiple doses of vials 220 containing the frozen biologic drug described herein. Storage chamber 210 is within cooling unit 230. Cooling unit 230 can include a variety of cooling processes, and preferably maintains the biologic drug in vials 220 at the desired temperature, for example, about −70° C. Vending machine 200 also includes power cord 214 that connects to a power source. Vending machine 200 includes system 300 capable of having a secure internet connection. System 300 can be, for example, a computing system with a secure internet connection. The internet connection is capable of communicating with computer 340 at a remote location. The remote location can be, for example, in the next room, across the country or across the world. System 300 is capable of accessing patient information about a specific patient and transmitting the information to computer 340 at remote location. System 300 may be configured to access patient information in a variety of ways including from removable data storage components such as a flash drive or zip drive or from accessing a network or a computer at the point-of-care site that has the patient information. System 300 may include, for example, keypad 310, display screen 320 and start button 330. A worker at the remote location can review the patient information and if satisfactory, can approve the patient for receiving a dose of biologic drug in vial 220. Once the patient is approved, computer 340 at a remote location can transmit authorization. Authorization can be verbal to a health worker from a worker at the remote location. Verbal authorization can simply instruct the health worker to press start button 330 to initiate the processing cycle. Alternatively, the health worker may be given a code to enter into keypad 310 to initiate the processing cycle. Display screen 320 may display the status of vending machine 200, for example, it may display "processing sample", "washing sample", etc. Alternatively, authorization can be by means of transmittal of a processing cycle initiation code directly to system 300 of vending machine 200 from computer 340.

In vending machine 200, upon receiving a start or initiation signal, vial 220 is moved to thawing chamber 240 in processing compartment 236. In thawing chamber 240, vial 220 is thawed to form thawed sample 220a. Thawing chamber 240 has the appropriate components and/or materials necessary for thawing a biological sample. Chambers 250, 260, and 270 can be washing, incubating and formulating chambers, respectively. Chambers 250, 260 and 270 also have the appropriate components and/or materials necessary for carrying out their respective processing steps. The samples in vials 220*b*, 220*c* and 220*d* are washed sample, incubated sample and formulated sample, respectively. Once the sample is formulated, it is moved to dispensing chamber 280. Vial 220*e* in dispensing chamber 280 can be removed and is ready for administration to the patient. Generally, the formulated sample is administered to the patient immediately or as quickly as possible. Preferably, the sample is administered to the patient within 4 hours of formulation. The biologic activity of the sample can decrease with time after the formulation of the sample.

Chambers 240, 250, 260 and 270 can be any type of chambers, i.e. thawing, washing, mixing, and can be specific to the specific requirements of the biologic drug stored in vending machine 200. Embodiments are also contemplated wherein vending machine 200 includes only one chamber for all of the processing and the different steps in the processing are conducted while the sample is in the one chamber.

A variety of biologic drugs can be manufactured, stored and dispensed using the devices and methods described herein. In an exemplary embodiment, the manufacturing of a biologic drug at a remote facility includes obtaining T-cells from a healthy donor and differentiating these T-cells ex vivo. The ex vivo preparation of cells can include engagement of the CD3 and CD28 cell surface proteins through cross-linking, for example, by anti-CD3 and anti-CD28 antibodies as described in, for example, U.S. Pat. No. 7,435,592. The ex vivo prepared cells can be frozen prior to transporting to a point of care facility.

At the point of care facility, the frozen ex vivo prepared T-cells can be stored in an automated device and processed or formulated for administration upon receipt of authorization or approval of a patient for the biologic drug. The processing includes thawing the biologic drug and reactivating just prior to administration to a patient. The reactivation of the cells can be as described in U.S. Pat. No. 7,402,431. Briefly, the frozen cells can be thawed and reactivated by engaging cell surface proteins CD3 and CD28. The reactivation can include cross-linking the CD3 and CD28 proteins with, for example, anti-CD3 and anti-CD28 monoclonal antibodies. In some embodiments, the anti-CD3 and anti-CD28 monoclonal antibodies are attached to biodegradable particles. These reactivated allogeneic T-cells produce interferon-gamma and express high density CD40L on the cell surface.

The biologic drug stored and processed in automated devices described herein exhibit a substantial amount of biological activity. The amount of biological activity exhibited can vary and depend on the length of storage, the conditions of transport and storage, the specific biologic activity and the nature of the living cells. Preferably, the biologic drugs described herein, upon formulation, exhibit at least about 50% of the biologic activity relative to the activity of the biologic drug formulated at a manufacturing facility. More preferably, the biologic drugs exhibit at least about 80 percent of the activity, and even more preferably, at least about 95 percent of the activity after processing compared to a biologic processed at the manufacturing facility.

Although the present invention has been described with reference to preferred embodiments, workers skilled in the art will recognize that changes may be made in form and detail without departing from the spirit and scope of the invention.

What is claimed is:

1. A method for dispensing a biologic drug comprising:
storing the biologic drug in an automated device under desired conditions; and
processing the biologic drug in the automated device upon receipt of authorization to process drug, wherein the automated device comprise, a storage chamber in a cooling unit for storing one or more doses of a biologic drug; a processing compartment within the automated device comprising one or more chambers for processing the one or more doses of the biologic drug, wherein the processing compartment comprises apparatus and materials in the one or more chambers for formulation of the biologic drug prior to administration to a patient; a system for receiving authorization to move the one or more doses of the biologic drug from the storage chamber to the one or more chambers of the processing compartment; and a dispensing chamber for receiving the biologic drug from the processing compartment.

2. The method of claim/wherein the biologic drug is manufactured at a remote location, stored for long term storage and transported for placement in the automated device.

3. The method of claim/wherein the biologic drug is stored at about −70° C.

4. The method of claim/wherein authorization comprises approval of a patient for receiving the biologic drug.

5. The method of claim 1 wherein the authorization step comprises receiving authorization from a remote computer through an internet connection in the automated device.

6. The method of claim 1 wherein the processing comprises thawing, washing, mixing, crosslinking, incubating, formulating and combinations thereof.

7. The method of claim 1 wherein the biologic drug regains biological activity after the processing.

8. The method of claim 1 wherein the biologic drug comprises living cells.

9. The method of claim 1 wherein the biologic drug comprises immune cells.

10. The method of claim 1 wherein the biologic drug comprises activated T-cells.

11. The method of claim 1 wherein the biologic drug comprises activated T-cells and processing comprises reactivation of the T-cells prior to administration to a patient.

12. A method for providing a biologic drug comprising:
manufacturing the biologic drug in a manufacturing facility;
transporting the biologic drug to a point of care site wherein the biologic drug is transported under conditions to maintain the biologic activity of the drug; and
storing the biologic drug in an automated device at the point of care site until a patient is authorized for receiving the biologic drug, wherein the automated device comprises a storage chamber in a cooling unit for storing one or more doses of a biologic drug; a processing compartment within the automated device comprising one or more chambers for processing the one or more doses of the biologic drug, wherein the processing compartment comprises apparatus and materials in the one or more chambers for formulation of the biologic drug prior to administration to a patient; a system for receiving authorization to move the one or more doses of the biologic drug from the storage chamber to the one more chambers of the processing compartment; and a dispensing chamber for receiving the biologic drug from the processing compartment.

13. The method of claim 12 wherein the method further comprises processing the biologic drug in the automated device for administration to a patient.

14. The method of claim 12 wherein the biologic drug is frozen after manufacturing and remains frozen during transportation to the point of care site.

15. The method of claim 12 wherein the biologic drug comprises living cells.

16. The method of claim 12 wherein the automated device comprises a computing system with an internet connection to transfer patient data and receive authorization to process the biologic drug for administration.

\* \* \* \* \*